US009375576B2

United States Patent
Pitman

(10) Patent No.: US 9,375,576 B2
(45) Date of Patent: *Jun. 28, 2016

(54) METHOD AND APPARATUS FOR THE TREATMENT OF FOCAL DYSTONIA

(71) Applicant: Michael J. Pitman, New York, NY (US)

(72) Inventor: Michael J. Pitman, New York, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 14/794,522

(22) Filed: Jul. 8, 2015

(65) Prior Publication Data

US 2015/0306400 A1  Oct. 29, 2015

Related U.S. Application Data

(63) Continuation of application No. 13/854,031, filed on Mar. 29, 2013, now Pat. No. 9,095,707.

(60) Provisional application No. 61/617,537, filed on Mar. 29, 2012.

(51) Int. Cl.
*A61N 1/36* (2006.01)

(52) U.S. Cl.
CPC ........ *A61N 1/36164* (2013.01); *A61N 1/36003* (2013.01); *A61N 1/36057* (2013.01); *A61N 1/36067* (2013.01); *A61N 1/36171* (2013.01); *A61N 1/36175* (2013.01); *A61N 1/3601* (2013.01)

(58) Field of Classification Search
None
See application file for complete search history.

(56) References Cited

U.S. PATENT DOCUMENTS

| 6,892,098 | B2 | 5/2005 | Ayal et al. |
| 8,838,252 | B2* | 9/2014 | Pitman .......................... 607/62 |
| 9,095,707 | B2* | 8/2015 | Pitman |
| 2003/0100933 | A1 | 5/2003 | Ayal et al. |
| 2004/0024439 | A1 | 2/2004 | Riso |
| 2008/0119898 | A1 | 5/2008 | Ben-David et al. |
| 2008/0208284 | A1 | 8/2008 | Rezai et al. |
| 2009/0187124 | A1 | 7/2009 | Ludlow et al. |
| 2011/0178529 | A1 | 7/2011 | Muller et al. |
| 2013/0261699 | A1 | 10/2013 | Pitman |
| 2013/0261705 | A1 | 10/2013 | Pitman |

OTHER PUBLICATIONS

Aronson, A.E. et al., "Adductor spastic dysphonia: three years after recurrent laryngeal nerve resection", Laryngoscope, Jan. 1983; 93(1): 1-8. Retrieved Aug. 5, 2013 from PubMed.

Aviv, J.E. et al., "Overcoming laryngospasm by electrical stimulation of the posterior cricoarytenoid muscle", Otolaryngol Head Neck Surg., Feb. 1989; 100(2): 110-8. Retrieved Aug. 2, 2013 from PubMed.

Berke, G.S. et al., "Selective laryngeal adductor denervation-reinnervation: a new surgical treatment for adductor spasmodic dysphonia", Ann Otol Rhino Laryyngol, Mar. 1999; 108(3): 227-31. Retrieved Aug. 5, 2013 from PubMed.

Bidus, K. et al., "Effects of Adductor Muscle Stimulation on Speech Abductor Spasmodic Dysphonia", Laryngoscope 110: Nov. 2000; pp. 1943-1948.

(Continued)

*Primary Examiner* — Carl H Layno
*Assistant Examiner* — Jon Eric C Morales
(74) *Attorney, Agent, or Firm* — Schwabe, Williamson & Wyatt, P.C.

(57) ABSTRACT

A method and apparatus for using low levels of electrical stimulation to treat focal dystonia by stimulating the afferent nervous system and/or altering the function of the gamma motor neurons innervating muscles which experience symptomatic spasms.

29 Claims, 4 Drawing Sheets

(56) References Cited

OTHER PUBLICATIONS

Bielamowica S. et al., "Effects of botulinum toxin on pathophysiology in spasmodic dysphonia", Ann Otol Rhinol Laryngol, Feb. 2000; 109(2): 194-203. Retrieved Aug. 5, 2013 from PubMed.
Biller H.F. et al., "Laryngeal nerve crush for spastic dysphonia", Ann Otol Rhinol Laryngol, Sep.-Oct. 1983; 92(5 Pt 1): 469. Retrieved Aug. 5, 2013 from PubMed.
Blitzer A. et al., "Botulinum toxin (BOTOX) for the treatment of 'spastic dysphonia' as part of a trial of toxin injections for the treatment of other cranial dystonias", Laryngoscope, Nov. 1986; 96(11): 1300-1. Retrieved Aug. 5, 2013 from PubMed.
Blitzer A. et al.. "Botulinum toxin management of spasmodic dysphonia (laryngeal dystonia): a 12-year experience in more than 900 patients", Laryngoscope, Oct. 1998; 108(10): 1435-41. Retrieved Aug. 5, 2013 from PubMed.
Boroojerdi B. et al., "Effects of botulinum toxin on motor system excitability in patients with writer's cramp", AAN Enterprises, Inc.; Neurology 61; Dec. (1 of 2) 2003; pp. 1546-1550.
Chan S.W. et al., "Long-term results of type II thyroplasty for adductor spasmodic dysphonia", Laryngoscope, Sep. 2004; 114(9): 1604-8. Retrieved Aug. 5, 2013 from PubMed.
Chhetri O.K. et al., "Long-term follow-up results of selective laryngeal adductor denervation-reinnervation surgery for adductor spasmodic dysphonia", Apr. 2006, 116(4 ): 635-42. Retrieved Aug. 5, 2013 from PubMed.
Dedo H.H., "Recurrent laryngeal nerve section for spastic dysphonia", Ann Otol Rhinal Laryngol, Jul.-Aug. 1976; 85(4 Pt 1): 451-9. Retrieved Aug. 5, 2013 from PubMed.
Detrembleur C. et al., "Botulinum Toxin and Short-Term Electrical Stimulation in the Treatment of Equinus in Cerebral Palsy", Movement Disorders, vol. 17, No. 1, 2002; pp. 162-169.
Eleopra R. et al, "Botulinum neurotoxin serotype C: a novel effective botulinum toxin therapy in human", Neuroscience Letters 224 (Feb. 1997); pp. 91-94.
Foley-Nolan D. et al., "Post whiplash dystonia well controlled by transcutaneous electrical nervous stimulation (TEMS): case report", J Trauma, Jul. 1990: 30(7): 909-10. Retrieved Aug. 2, 2013 from PubMed.
Hallett M., "How does botulinum toxin work?", Ann Neural., Jul. 2000; 48(1):7-8. Retrieved Aug. 5, 2013 from PubMed.
Kaji R. et al., "Tonic vibration reflex and muscle afferent block in writer's cramp", Ann Neural, Aug. 1995; 38(2): 155-62. Retrieved Aug. 2, 2013 from PubMed.
Kerr C. et al., "Electrical stimulation in cerebral palsy: a randomized controlled trial", Developmental Medicine & Child Neurology, 2006; 48: pp. 870-876.
Kaufman J.A. et al.. "Treatment of adductor-type spasmodic dysphonia by surgical myectomy: a preliminary report", Ann Otol Rhinal Laryngol., Feb. 2006; 115(2): 97-102. Retreived Aug. 5, 2013 from PubMed.
Leis A.A. et al., "Modification of cervical dystonia by selective sensory stimulation", J Neural Sci., Jul. 1992; 110(1-2): 79-89. Retrieved Aug. 2, 2013 from PubMed.
Lim E. C. H. et al., "Botulinum Toxin-A injections via electrical motor point stimulation to treat writer's cramp: Pilot study", Neurology, Neurophysiology and Neuroscience, 2006:4 (Jun. 30, 2006); pp. 1-7.
Liu X. et al., "The sensory and motor representation of synchronized oscillations in the globus pallidus in patients with primary dystonia", Brain (2008), 131; pp. 1562-1573.
Ludlow t al., "Successful treatment of selected cases of abductor spasmodic dysphonia using botulinum toxin injection", Otolaryngol Head Neck Surg., Jun. 1991; 104(6): 849-55. Retrieved Aug. 5, 2013 from PubMed.
Miller R.H. et al., "Botulinum toxin injection of the vocal fold for spasmodic dysphonia. A preliminary report", Arch Otolaryngol Head Neck Surg., Jun. 1987; 113(6): 603-5. Retrieved Aug. 5, 2013 from PubMed.
Murry T. et al., "Combined-modality treatment of adductor spasmodic dysphonia with botulinum toxin and voice therapy", J Voice, Dec. 1995; 9(4): 460-5. Retrieved Aug. 5, 2013 from PubMed.
Nash E.A. et al., "Laryngeal muscle activity during speech breaks in adductor spasmodic dysphonia", Laryngoscope, Apr. 1996; 106(4): 484-9. Retrieved Aug. 5, 2013 from PubMed.
Olver J. et al., Botulinum toxin assessment, intervention and aftercare for lower limb disorders of movement and muscle tone in adults: international consensus statement:, European Journal of Neurology 2010, 17 (Suppl. 2): pp. 57-73.
Opaysky R. et al., "Somatosensory Cortical Activation in Cervical Dystonia and its Modulation with Botulinum Toxin: An fMRI Study", International Journal of Neuroscience, 122, 2012; pp. 45-52.
Parnes S.M. et al., "Study of spastic dysphonia using videofiberoptic laryngoscopy", Ann Otol Laryngol., May-Jun. 1978; 87(3) (3pt1 ): 322-6. Retrieved Aug. 5, 2013 from PubMed.
Pitman M.J. et al., "Clinical Investigation Plan Feasibility Study, Treatment of Spasmodic Dysphonia", Clinical Investigation 2012CIP001; Jun. 15, 2012; pp. 1-60.
Quartarone A. et al., "Enhanced Long-Term Potentiation-Like Plasticity of the Trigeminal Blink Reflex Circuit in Blepharospasm", The Journal of Neuroscience, Jan. 11, 2006; 26(2): pp. 716-721.
Sanuki T. et al., "Overall evaluation of effectiveness of type II thyroplasty for adductor spasmodic dysphonia", Laryngoscope, Dec. 2007; 117(12):2244-9. Retrieved Aug. 5, 2013 from PubMed.
Sercarz JA et al., "Bilateral thyroarytenoid denervation: a new treatment for laryngeal hyperadduction disorders studied in the canine", Otolaryngol Head Neck Surg., Nov. 1992; 107(5): 657-68. Retrieved Aug. 5, 2013 from PubMed.
So A. et al., "Alterations in CNS activity induced by botulinum toxin treatment in spasmodic dysphonia: an H2150 PET study", J Speech Lang Hear Res., Oct. 2006; 49(5): 1127-46. Retrieved Aug. 5, 2013 from PubMed.
Tinazzi M. et al., "Effects of transcutaneous electrical stimulation on motor cortex excitability in writer's cramp: neurophysiological and clinical correlations", Mov Disord., Nov. 2006; 21 ( 11 ): 1908-13. Retrieved Aug. 5, 2013 from PubMed.
Tinazzi M. et al., "Long-lasting modulation of human motor cortex following prolonged transcutaneous electrical nerve stimulation (TEMS) of forearm muscles: evidence of reciprocal inhibition and facilitation", Exp Brain Res., Mar. 2005; 1561(4): 457-64. Retrieved Aug. 5, 2013.
Tinazzi M. et al., "TENS for treatment of writer's cramp dystonia: A randomized, placebo-controlled study", Neurology, 2005; 64: pp. 1946-1948.
Toglia J. et al., Treatment of myoclonic dystonia with transcutaneous electrical nerve stimulation: I tal. J. Neurol. Sci VI: 1985; pp. 75-78.
Sulica L., Contemporary management of spasmodic dysphonia:, Curr Opin Otolaryngol Head Neck Surg., Dec. 2004; 12(6): 543-8. Retrieved Aug. 5, 2013.
Wissel J. "Multidisciplinary therapy for focal spasticity treatment", Nervenarzl., Jun. 2008; 79 Suppl1 :24-8. Retrieved Apr. 19, 2013.

\* cited by examiner

METHOD AND APPARATUS FOR THE TREATMENT OF FOCAL DYSTONIA

CROSS-REFERENCE TO RELATED APPLICATIONS

This application is a Continuation of U.S. application Ser. No. 13/854,031, filed Mar. 29, 2013, entitled "METHOD AND APPARATUS FOR THE TREATMENT OF SPASMODIC DYSPHONIA," which in turn claimed priority to U.S. Provisional Patent Application No. 61/617,537, entitled "METHOD AND APPARATUS FOR THE TREATMENT OF SPASMODIC DYSPHONIA" filed on Mar. 29, 2012, both of which are hereby incorporated by reference in their entirety for all purposes.

TECHNICAL FIELD

The present disclosure relates to methods and apparatus for the treatment of focal dystonia.

BACKGROUND

Focal dystonias are neurological movement disorders characterized by involuntary muscle contractions causing spasms, twisting, repetitive movements, or abnormal postures. Focal dystonias include cervical dystonia, blepharospasm, focal hand dystonia, and spasmodic dysphonia. These disorders can significantly impact quality of life.

Treatment of dystonia has focused on inhibiting the action of alpha motor neurons which cause the muscles to contract in spasm. For example, historically treatment of spasmodic dysphonia has been aimed at paralyzing or weakening one of the vocal folds in order to decrease its ability spasm and interrupt phonation. Dedo first proposed and popularized recurrent laryngeal nerve resection as a treatment for spasmodic dysphonia. This was the first and only surgical procedure which achieved widespread use. Some surgeons did not want to completely transect the RLN, and instead crushed it to weaken or paralyze the vocal folds but keep the nerve intact. Unfortunately, over the long term, the majority of patients who underwent either resection or crush experienced a return of their phonatory spasms. Due to this, both procedures were eventually abandoned.

Botulism toxin (BTX) injection is a common and "gold standard" treatment of dystonia. BTX inhibits neural function, and it is thought that it controls the symptoms of dystonia by preventing the firing of overactive motor neurons.

A few researchers have attempted to use electrical nerve stimulation to treat the symptoms of dystonia. Bidus, et al explored the use of electrical nerve stimulation to treat abductor spasmodic dysphonia by stimulating the motor nerves to the adductor muscle, causing an antagonistic muscle contraction designed to counteract the spasms caused by the disorder.

Tinazzi et al attempted to use low frequency transcutaneous electrical nerve stimulation (TENS) to treat spasms associated with writers' cramp. TENS was delivered to forearm flexor muscles of ten individuals suffering from writers' cramp at a level of stimulation that was below the threshold to cause muscular contractions. The researchers concluded that the TENS treatment may have therapeutic effects on writers' cramp dystonia that lasts for several weeks. The researchers attributed this therapeutic effect to a reshaping of reciprocal excitatory and inhibitory functions between agonist and antagonist muscles, observing that those functions are typically severely impaired in dystonia. Specific muscles were not targeted in this therapy, both because the researchers intended to restore the relationship between agonist and antagonist muscles, which teaches away from the specific targeting of muscles, and because the use of TENS made specific targeting impossible.

Apart from these efforts, the use of electrical nerve stimulation has been primarily used to reanimate paralyzed muscle, not to treat spasmodic disorders such as focal dystonia.

DETAILED DESCRIPTION OF DISCLOSED EMBODIMENTS

As discussed above, the general belief is that symptoms of focal dystonia result from abnormal motor signals to motor neurons which control the muscles. Abnormal motor neural activity causes muscles to spasm, resulting in the symptoms of focal dystonia. Within this paradigm it is assumed that BTX is effective because it interferes with the motor nerves innervating the muscle into which it has been injected, and thus interferes with the muscle's ability to spasm. The central nervous system continues to send abnormal motor signals to motor neurons, but they are unable to cause muscle contractions as forcefully.

The inventor has realized that contrary to conventional thinking, focal dystonias are more likely caused by abnormal afferent nerve signals and not abnormal motor nerve signals.

Efferent nerves, also known as motor neurons, carry nerve impulses from the central nervous system to effectors such as muscles. They are involved in muscular control. Afferent neurons, also known as receptor neurons, carry nerve impulses to the central nervous system. Signals carried by afferent nerves create sensations that the brain then identifies as pain, itch, stretch, etc.

Figure 4:
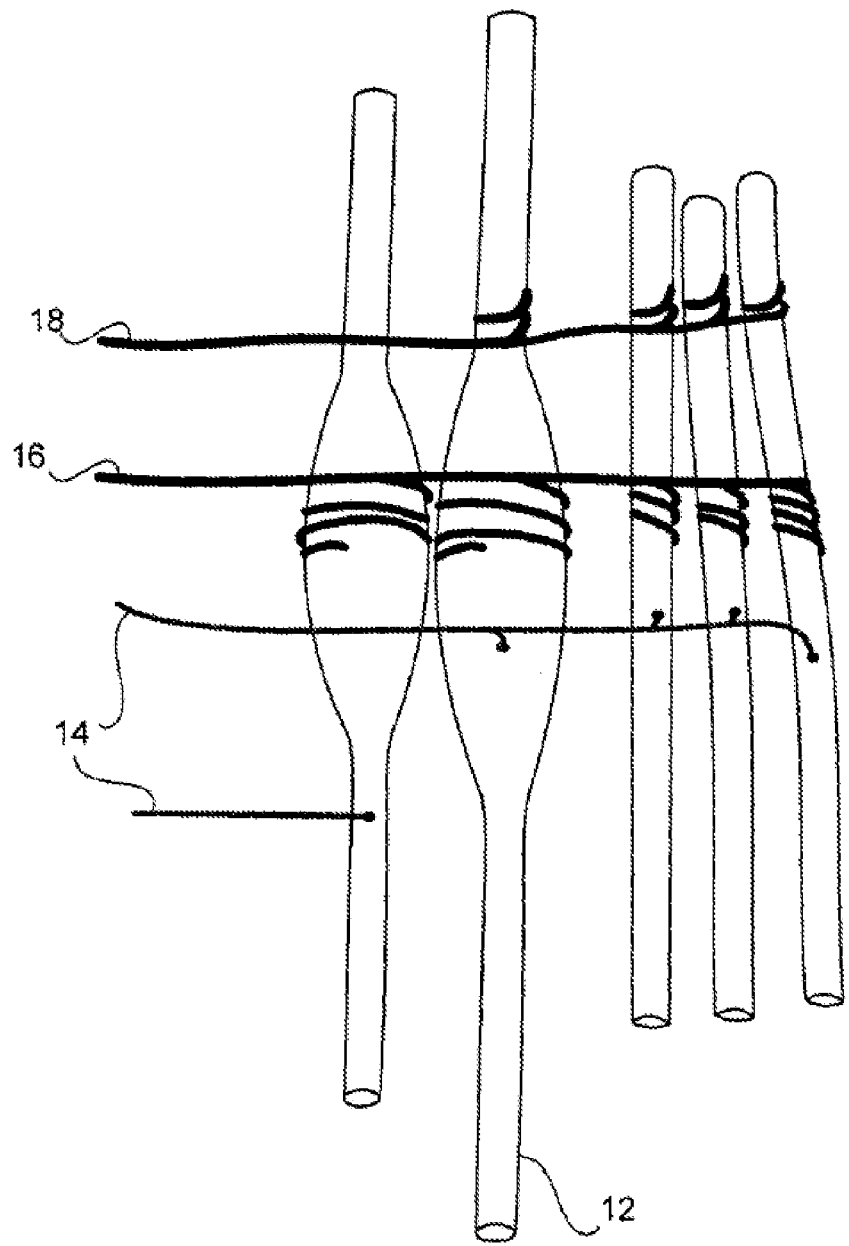
FIG. 4 is a cut away view of a muscle spindle.
Figure 5:
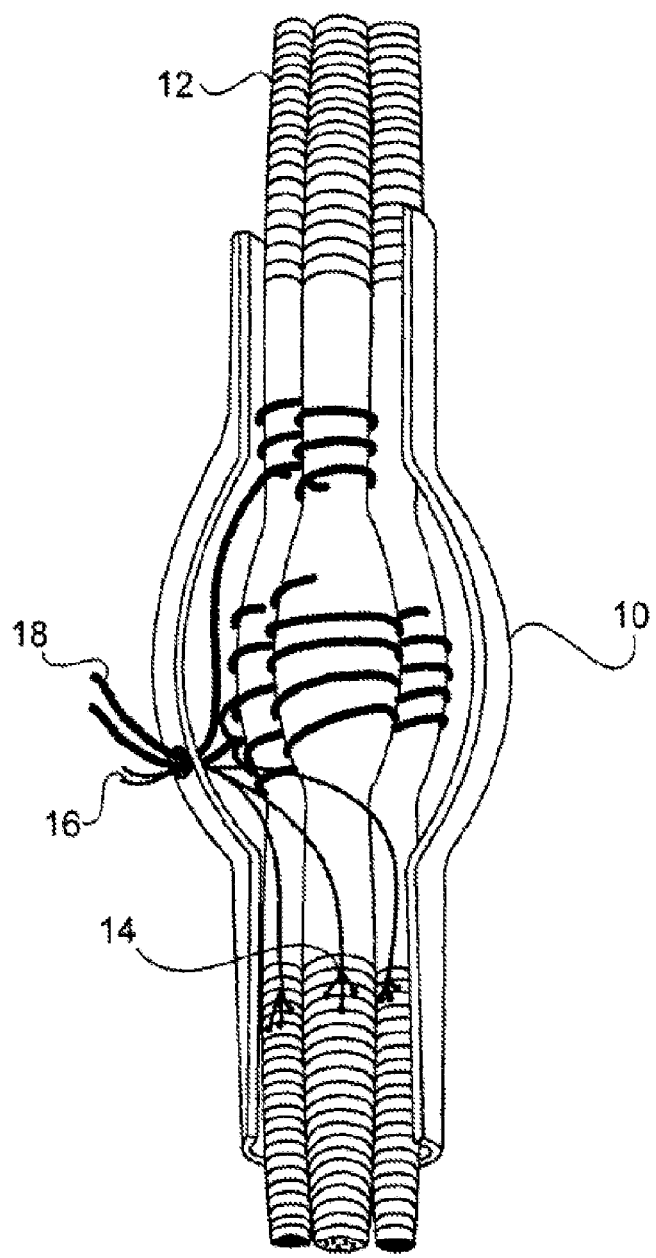
FIG. 5 is a muscle view of a muscle spindle.

As shown in FIGS. 4 and 5, muscle spindles 10 consist of both gamma motor neurons and afferent (sensory) neurons and are an important component of muscular proprioception. The intrafusal muscle fibers 12, are innervated by type Ia 16 and type II 18 sensory afferent neurons. They lie parallel to the extrafusal muscle fibers and are innervated with afferent nerves which sense muscle length and rate of changes in muscle length. The gamma motor neuron 14 also innervates the intrafusal fibers 12 of the muscle spindle 10. By causing contraction of the intrafusal muscle fibers, the gamma motor neuron increases the sensitivity of the afferent neurons of the muscle spindle. When alpha neurons fire and cause the muscles to contract the muscle spindles shorten and become slack, and lose their ability to detect muscle length. To prevent this, when the central nervous system sends signals via alpha neurons, co-activating signals are also sent to the gamma motor neurons 14. The gamma motor neurons maintain tautness of muscle spindles even as a muscle contracts, and permit the muscle spindles to detect muscle length. Gamma neuron activity is further modulated by input form the type Ia and type II afferent nerves as they sense changes in muscle length. Thus, the gamma neurons set the sensitivity of muscle spindles.

The consistent level of gamma activity is called gamma bias. Overactive gamma neurons with a high bias result in hyper-sensitivity of the afferent nerves of the muscle spindle. As a result, muscle contractions are inappropriately increased, resulting in a muscle spasm.

Smaller neurons require a smaller amount of stimulation to reach their excitability thresholds than larger neurons do, and gamma neurons are smaller than alpha neurons. As a result, gamma neurons may fire in response to a given stimulus where alpha neurons subjected to the same stimulus do not.

As discussed above, it is believed that the symptoms of spasmodic dysphonia result from abnormal motor signals from motor neurons which control the muscles the larynx. Abnormal motor neuron activity causes the muscles to spasm, resulting in SD. This understanding of SD has led to treatments which seek to denervate the larynx, surgically or chemically. It is believed that BTX is effective because it weakens the muscle into which it is injected, and that the weakening effect interferes with the muscle's ability to spasm. The muscles continue to receive abnormal motor signals from their innervating motor neurons, but they are able to respond less forcefully.

However, the inventor has realized that, contrary to the conventional thinking, spasmodic dysphonia may be caused by abnormal afferent nerve signals and not abnormal motor signals. Abnormal afferent nerve signals which originate in the larynx cause abnormal motor signals which in turn cause the muscles to spasm. BTX inhibits the function of motor nerves by preventing nerves from releasing acetycholine at the synaptic junction. BTX may work on the gamma motor neurons in the muscle spindle in much the same way as it works on the alpha motor neurons, in that it decreases activity of both types of nerves via the same mechanism.

Neuromuscular stimulation, on the other hand, is often used to increase neurologic activity, in other words, cause muscles to contract, e.g., in order to treat paralysis or paresis. The use of neuromuscular stimulation to impact the afferent nervous system is different in both objects and methodology. For example, it is well accepted that the application of electrical stimulation to a muscle will cause that muscle to contract when the stimulation rises above the excitability threshold of the innervating motor neurons. However, the effects of stimulation on the afferent system are less predictable. Tinazzi, et. al observed that high frequency stimulation of peripheral cutaneous nerves for ten minutes in normal subjects produced a decrease in sensorimotor cortex excitability lasting about 60 minutes, but low frequency stimulation (10 Hz) of peripheral nerves of normal subjects for 2 hours produced an increase in sensorimotor cortex excitability lasting 30 to 40 minutes. To the inventor's knowledge, no one has observed a mechanism whereby electrical stimulation is used to lower the activity of motor neurons through the stimulation of the sensory system.

The inventor has realized that subjecting a muscle to a low level of electrical stimulation functions as a sensory trick, acting on the afferent nervous system to changing the sensory milieu and interrupting abnormal sensory signaling to the brain, in turn alleviating spasmodic symptoms. Sensory tricks tend to lose their effectiveness over time. However, the parameters of electrical stimulation can be altered dynamically, and therefore it can better maintain its effectiveness.

Figure 2:
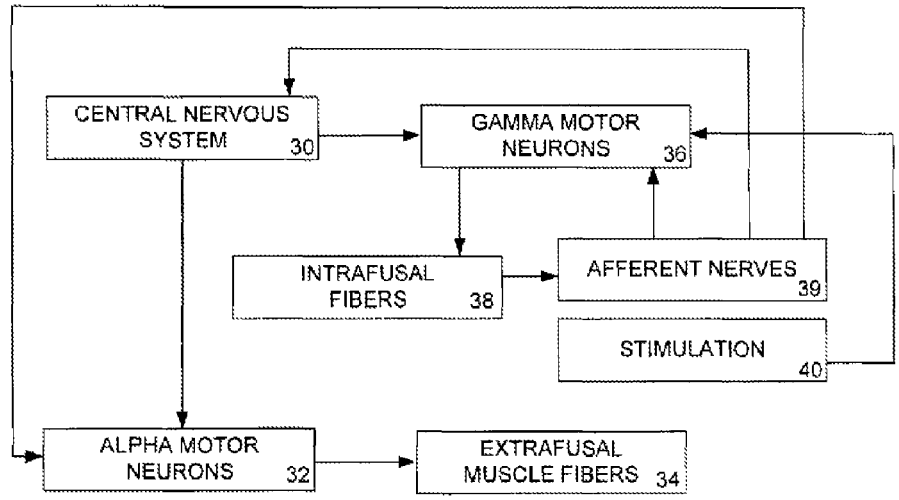
FIG. 2 is a flow chart illustrating the direction of impulses communicated between the central nervous system, the motor neurons, the muscles, the afferent nerves, and the gamma neurons and the impact of stimulation on gamma motor neurons.

The inventor has also realized that a relatively low level of electrical stimulation can alter the gamma loop, reducing the sensitivity of afferent nerves of the muscle spindle and causing a reduction in abnormal sensory signaling. As shown in FIG. 2, the central nervous system 30 sends impulses to alpha motor neurons 32, which act on extrafusal muscles fibers 34. The central nervous system simultaneously sends impulses to the gamma motor neurons 36, which act on the intrafusal muscle fibers 38 of the muscle spindles. The gamma motor neurons 36 are coactivated with the alpha motor neurons 34 to maintain an appropriate level of sensitivity in the muscle spindle sensory afferent nerves. The intrafusal muscle fibers act on the afferent nerves 39 in the muscle spindles. The afferent nerves 39 send impulses to the central nervous system, and possibly the alpha motor neurons 30 and the gamma motor neurons 36. Electrical stimulation 40 of the gamma motor neurons 36 changes how the gamma motor neurons 36 act on the intrafusal fibers 38 and hence alters the sensitivity of the afferent neurons. Inhibiting the gamma neuron 36 via electrical stimulation 40 will result in a decreased gamma motor neuron bias and will reset the muscle spindle sensory afferent neurons to a lower sensitivity. The high gain of the system will be decreased, and when an alpha motor neuron sends a signal for the extrafusal muscle fibers to contract, the system will no longer be hypersensitized, and the motor neuron signal will result in an appropriate contraction, not an uncontrolled spasm. Thus, a low level of electrical stimulation can provide a means of decreasing gamma motor neuron bias, thus utilizing electrical stimulation to decrease alpha motor neural activity and reduce spasm.

Figure 3:
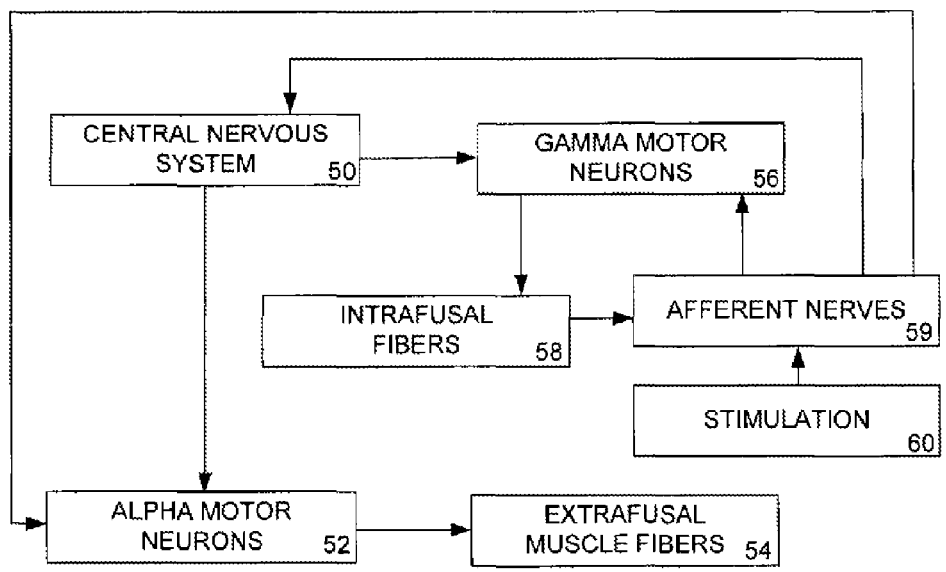
FIG. 3 is a flow chart illustrating the direction of impulses communicated between the central nervous system, the motor neurons, the muscles, the afferent nerves, and the gamma neurons and the impact of stimulation on the afferent system.

The inventor has also discovered that electrical stimulation can alter the gamma motor loop by stimulating the afferent neurons, thus utilizing afferent nerve stimulation to alter abnormal alpha motor neuron activity to effectively reduce muscle spasm, as shown in FIG. 3. The central nervous system 50 sends impulses to alpha motor neurons 52, which fire, causing extrafusal muscle fibers 54 to contract. The central nervous system simultaneously sends impulses to the gamma motor neurons 56, which act on the intrafusal muscle fibers 58 of the muscle spindles. This coactivation of the gamma motor neurons and the alpha motor neurons 54 maintain an appropriate level of sensitivity in the sensory afferent neurons of the muscle spindle. The intrafusal fibers act on the afferent nerves 59 innervating the intrafusal fibers 58 of the muscle spindle, which may send signals to the gamma and alpha motor neurons and the central nervous system 50. Stimulation of the afferent nerves innervating the intrafusal fibers 58 in the muscle spindles may directly alter the afferent-efferent loop, decreasing muscle spasm.

Low level, or afferent stimulation, as disclosed herein involves subjecting a muscle to an electrical impulse delivered by an electrode placed near, in contact with, or within the muscle. The stimulating electrical impulse may vary by parameter such as duration, amplitude, frequency, and/or duty cycle. These parameters are set and governed using a processor which is operably connected with one or more electrodes which are used to administer the stimulating electrical impulse. The duty cycle is the duration of time in which an impulse is being delivered relative to the duration of time in which no impulse is being delivered. An interrupted, or non-continuous pattern of stimulation alternates periods of delivery of an impulse with periods in which no impulse is being delivered. The duty cycle can be varied automatically by the processor. Additionally, the patient or individual directing treatment may turn the stimulator on or off as needed, resulting in an additional source of variation of stimulation.

Figure 1:
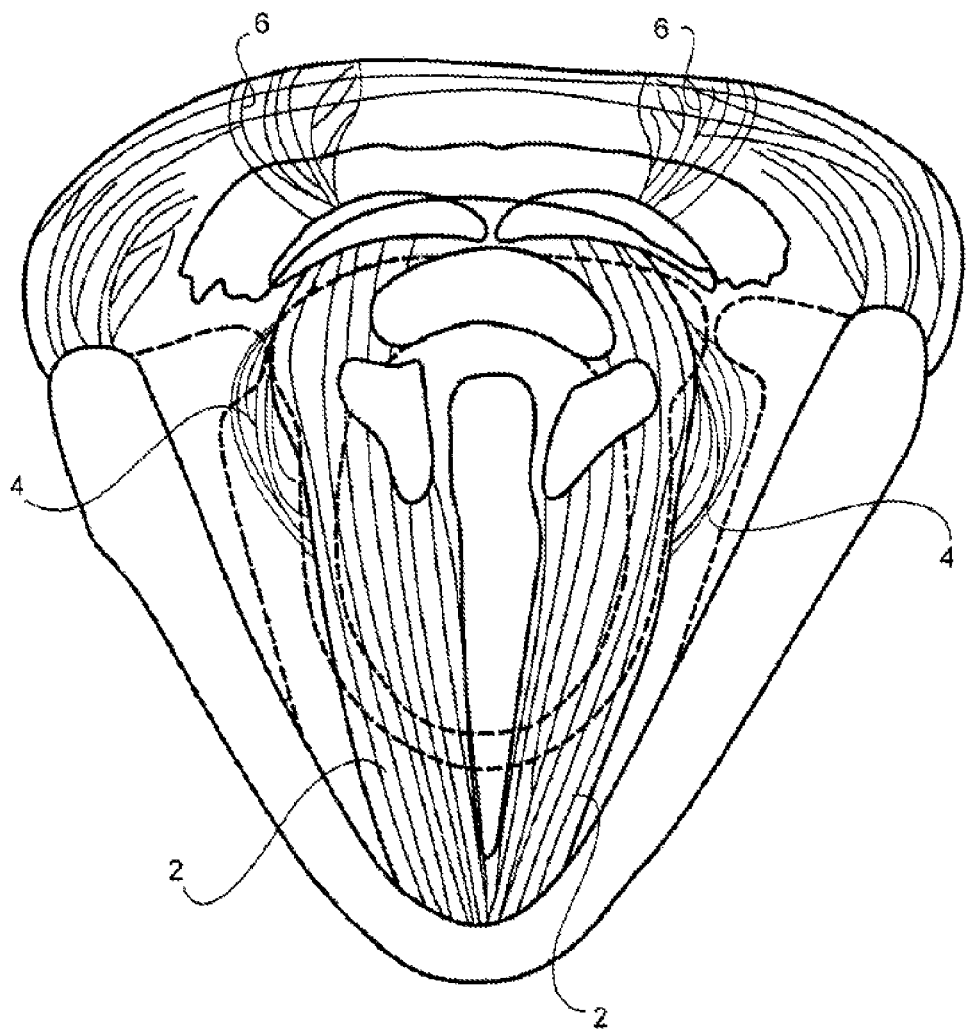
FIG. 1 shows a top view of the larynx.

This stimulating electrical impulse should preferably be delivered to the specific muscles that undergo symptomatic contraction, and effects to other structures should be minimized. The electrode or electrodes used to provide stimulation should be associated with or placed in communication directly with a muscle to be stimulated in a manner that limits its impact substantially to that muscle. This can be accomplished, for example, by placing electrodes in direct contact with the muscles which experience symptomatic spasm, for example the thyroartenoid (TA) 2, lateral cricoarytenoid 4, interarytenoid or posterior cricoarytenoid 6 muscles in spasmodic dysphonia, as shown in FIG. 1. This placement prevents unspecific stimulation of adjacent structures, and thereby prevents alteration of normally functioning sensory pathways in adjacent structures.

To treat dystonia, the active end of the stimulator should be placed in communication with or within the affected muscle and used to provide a stimulating signal or impulse at an amplitude and/or frequency that is below the excitation threshold of the alpha motor nerves innervating the muscle, and thus too low to cause firing of alpha nerves innervating the muscle fibers, and too low to cause muscle contractions. This stimulating electrical signal is sensed by the afferent nerves, causing interruption of the abnormal afferent-efferent loop that results in laryngeal spasms and the symptoms of dystonia. Additionally or alternatively, the signal impacts the function of the gamma loop, resetting gamma bias, and desensitizing the muscle spindle, resulting in less excitability and less responsiveness to muscle contractions and other stimuli. The muscle spindle's abnormal afferent signaling will be reduced or eliminated, resulting in normal signals to the alpha motor neurons which will result in normal phonation and instead of vocal spasms.

The electrical stimulation can be produced by a commercially available neurostimulator using electrodes that are inserted into the muscle most affected by dystonia using thin hypodermic needles. The level of stimulation delivered should be directed to the afferent nerves and the gamma motor neuron, and should be sufficiently weak that it does not produce muscle contractions by stimulating alpha motor neurons. Signals that are too weak to stimulate alpha motor neurons can nonetheless stimulate the afferent nerves of the muscle spindle and/or disrupt the action of the gamma neuron, changing the sensory nerve activity and gamma bias, preventing spasms of the laryngeal muscles.

The inventor has confirmed this hypothesis by showing that this low-level neural stimulation applied to the TA muscle is effective in treating spasmodic dysphonia (SD). The inventor has conducted a study to determine the influence of on-target TA electric stimulation which has shown that it is safe and effectively relieves the symptoms of SD. In comparison with TENS stimulation or even with the BTX injection this type of stimulation will be more precise and will allow better fine-tuning depending on the individual characteristics and symptom grade of each patient.

Additionally, on-target TA stimulation prevents the unwanted response of the PCA muscle, responsible for vocal cord abduction or the unspecific stimulation of the CT muscles. In this respect, evaluation of the exclusive stimulation of the TA prevents biases and/or artifacts due to the unspecific stimulation of the contiguous muscles (i.e. PCA and CT).

The innovative treatment represents an on-target treatment for dystonia, thus it is expected to minimize the problems observed in other therapeutic methods due to their aspecificity. Additionally, a stimulator will allow better fine-tuning based on the individual needs of each patient and may become a sound alternative to the present symptom-relieving therapies in use for dystonia. Finally, while BTX requires repeat treatment with painful injections approximately every three months, the methods disclosed herein require the implantation of a stimulation device and no further invasive treatment. The dystonia can be essentially cured.

A first-in-human, one-arm, cross-over, exploratory, open-label, prospective, longitudinal and monocentric study has confirmed the safety and efficacy of this treatment as compared to the current gold standard for the treatment of SD (i.e. BTX injection) within the same patient, thus avoiding the occurrence of biases due to the so called "patient-specific effects". This is particular important in an observatory study in which individual characteristics may significantly affect the outcome and the total number of patients expected to comply with the selection criteria is low (currently a niche population). The wash-out period was 12 to 13 weeks. The introduction of the wash-out period was designed to minimize biases during the data analysis, due to overlapping effects between the two treatments.

At the BTX injection visit, patients' medical histories were reviewed, any necessary medical examinations and laryngovideostroboscopy was performed. Additionally, patents were taped reading the sentences constructed to stimulate vocal spasms (before and at multiple time periods after the BTX injection). Patients were also asked to fill out a Voice handicap index-10 and study-specific 5 point liked scale at similar time points. Laryngeal Electromyography (LEMG) is a medical procedure that records the electrical activity produced by laryngeal muscles in action. During LEMG, electrical activity is recorded, amplified, and displayed on a screen and played on a loudspeaker to allow visual and sound analysis. Specifically in this study, LEMG will be used to localize the TA for intramuscular injection of botulinum toxin and placement of the electrical stimulator.

During injection with BTX, the subject was asked to assume a comfortable position with slightly extended neck. The investigator inserted the needle electrode into the TA. The subject was then asked to phonate by saying /i/. Position of the needle tip was confirmed by sharp electrical activity upon sustained /i/ phonation. Once the needle tip was confirmed to be within the TA the botulinum toxin was injected.

The laryngvideostroboscopy served to record the natural status of the vocal folds as well as vocal fold motion and mucosal wave during phonation of /i/ at the normal speech frequency.

The on-target TA-specific electrical stimulation was delivered using a commercially available device (CareFusion SYNERGY N series 2 channel EMG & stimulation). The unit is a dual-channel bipolar device that supplies monophasic pulsed current.

Since regular needle electrodes do not consistently maintain their intra-muscular position over the course of 20 to 60 minutes due to movement of related tissue, hooked-wire electrodes were used. This decision was also made due to the reduced size of the TA muscle and its relatively high inaccessibility that make the use of surface electrodes unfeasible. Hooked-wire electrodes were made by passing 1 or 2 very thin wires through a hypodermic needle. The end of the wire at the tip of the needle was bent down to form a "hook". The needle was inserted into the muscle and pulled out so that the wire hooked around the muscle fibers, securely held in position.

Placement for the hook wire electrodes was into the thyroarytenoid muscle.

Position of the hooked electrodes was verified using recognized adductor tasks: increased muscle activity during prolonged phonation of /i/ vowels and a valsava. The stimulation was delivered according to the following parameters:

1) Frequency: nominal 50 Hz (range 20-200 Hz)

2) Impulse duration: nominal 200 (range 50-750) microseconds

3) Impulse amplitude: is set below pain threshold and is too low to cause muscular contraction, range from 0 to 3 mA (tolerance±10%)

4) Stimulation treatment duration: 60 minutes

5) Simultaneous laryngoscopy confirmed an absence of stimulation induced muscle contraction.

The stimulation was repeated five times on five consecutive days. Before and after each stimulation session subjects' answers to the likert scale and evaluation of taped readings of sentences constructed to stimulate vocal spasms showed that patients and trained listeners perceived improved voice quality compared to the baseline. After the 5 sessions of stimulation a Voice handicap index-10 was also completed by the patients, again showing decrease of their vocal handicap over the week. Carry over of vocal improvement lasted days to weeks and was rated again with a liked scale, taped reading and the Voice handicap index-10 at similar time periods as was performed after BTX injection. Improvement in symptoms indicated that a low level of electrical stimulation, too low to affect the alpha motor nerves, resulted in decreased vocal spasms, improvement in voice comparable to BTX injections and confirmed the efficacy of the stimulation mechanism described herein.

Stimulation delivered in accordance with the inventions disclosed herein should preferably be delivered in a varied pattern over time rather than in a continuous manner. Parameters such as frequency, amplitude, and duty cycle which are inherently governed by the processor or by patient manipulation of the processor duty cycle, should be varied. Patients may turn the stimulator on or off as needed for treatment.

It is suspected that the sensory nervous system and the central nervous system, will acclimate to a given level of constant stimulation and cause the stimulation to lose its effectiveness over time. Variation in the frequency, amplitude or duty cycle of the stimulating electrical impulse should be used to avoid acclimation.

The terms and expressions which have been used in this specification are intended to describe the invention, not limit it. The scope of the invention is defined and limited only by the following claims.

What is claimed is:

1. A method of treating focal dystonia comprising:
   a. providing a system comprising a stimulating electrode operably connected with a processor configured to set one or more stimulation parameters for an electrical impulse deliverable by the electrode;
   b. placing the electrode in contact with at least one neuron innervating at least one muscle;
   c. using the processor to set the stimulation parameters such that the electrical impulse causes a level of stimulation which does not exceed an excitability threshold of one or more alpha motor neurons located within the at least one muscle; and
   d. delivering the electrical impulse to the at least one neuron, wherein the electrical impulse acts upon one or more muscle spindles located within the at least one muscle.

2. The method of claim 1, wherein the electrical impulse has an amplitude, a frequency, and a duty cycle governed by the processor, and wherein at least one of the amplitude and the frequency and the duty cycle are varied during treatment.

3. The method of claim 1, wherein the electrical impulse acts upon one or more gamma motor neurons located within the at least one muscle.

4. The method of claim 3, wherein the stimulating electrical impulse decreases the level of activity of the one or more gamma motor neurons.

5. The method of claim 1, wherein the electrical impulse acts upon one or more afferent neurons located within the at least one muscle.

6. The method of claim 5, wherein the stimulating electrical impulse decreases the level of activity of the one or more afferent neurons.

7. The method of claim 5, wherein the stimulating electrical impulse inhibits at least one neural signal transmitted to a central nervous system by the one or more afferent neurons.

8. A method of treating focal dystonia comprising using an electrode in communication with a processor to deliver an electrical impulse to at least one neuron innervating at least one muscle, wherein the impulse delivers a level of stimulation that is below an excitability threshold of alpha motor neurons innervating the at least one muscle, and wherein the electrical impulse acts upon a gamma loop.

9. The method of claim 8, wherein the electrical impulse has an amplitude, a frequency, and a duty cycle governed by parameters set by the processor, and wherein at least one of the amplitude and the frequency and the duty cycle are varied during treatment.

10. The method of claim 8, wherein the electrical impulse acts upon one or more gamma neurons located within the at least one muscle.

11. The method of claim 10, wherein the electrical impulse decreases a level of activity of the one or more gamma neurons.

12. The method of claim 8, wherein the electrical impulse acts upon one or more afferent neurons located within the at least one muscle.

13. The method of claim 12, wherein the stimulating electrical impulse decreases the level of activity of the one or more afferent neurons.

14. The method of claim 12, wherein the stimulating electrical impulse alters or inhibits at least one neural signal transmitted to a central nervous system by the one or more afferent neurons.

15. The method of claim 8, wherein the electrical impulse acts on one or more gamma neurons located within the gamma loop.

16. The method of claim 8, wherein the electrical impulse acts upon one or more afferent neurons located within the gamma loop.

17. A system for treating focal dystonia comprising an electrode configured to deliver an electrical impulse to at least one neuron innervating at least one muscle, the electrode being in communication with a processor configured to set one or more stimulation parameters governing the electrical impulse, wherein the processor causes the electrical impulse to deliver a level of stimulation to the at least one neuron, the level of stimulation being below an excitability threshold of alpha neurons innervating the muscle, and wherein the electrical impulse acts upon one or more afferent neurons, and wherein electrical impulse acts upon one or more afferent neurons located within a gamma loop.

18. The system of claim 17, wherein the electrical impulse has an amplitude, a frequency, and a duty cycle governed by the one or more stimulation parameters, and wherein at least one of the amplitude and the frequency and the duty cycle are varied during treatment.

19. The system of claim 17, wherein the electrical impulse acts upon one or more gamma neurons located within the at least one muscle.

20. The system of claim 19, wherein the electrical impulse decreases a level of activity of the one or more gamma neurons.

21. The system of claim 17, wherein the electrical impulse decreases a level of activity of the one or more afferent neurons.

22. The method of claim 17, wherein the electrical impulse inhibits at least one neural signal transmitted to a central nervous system by the one or more afferent neurons.

23. A method of treating focal dystonia comprising:
 a. providing a system comprising a stimulating electrode operably connected with a processor configured to set one or more stimulation parameters for an electrical impulse deliverable by the electrode;
 b. placing the electrode in contact with at least one neuron innervating at least one muscle;
 c. using the processor to set the one or more stimulation parameters such that the electrical impulse causes a level of stimulation that does not exceed an excitability threshold of one or more alpha motor neurons located within the at least one muscle; and
 d. delivering the electrical impulse to the at least one neuron, wherein the electrical impulse acts upon a gamma loop.

24. The method of claim 23, wherein the electrical impulse acts upon one or more gamma motor neurons located within the gamma loop.

25. The method of claim 23, wherein the electrical impulse acts upon one or more afferent neurons located within the gamma loop.

26. A method of treating focal dystonia comprising:
 a. providing a system comprising a stimulating electrode operably connected with a processor configured to set one or more stimulation parameters for an electrical impulse deliverable by the electrode;
 b. placing the electrode in contact with at least one neuron innervating at least one muscle;
 c. delivering the electrical impulse to the at least one neuron, wherein the electrical impulse acts upon one or more afferent neurons located within the at least one muscle, and wherein electrical impulse acts upon one or more afferent neurons located within a gamma loop.

27. A system for treating focal dystonia comprising an electrode configured to deliver an electrical impulse to at least one neuron innervating at least one muscle, the electrode being in communication with a processor configured to set one or more stimulation parameters governing the electrical impulse, wherein the processor causes the electrical impulse to deliver a level of stimulation to a neuron placed in communication with the electrode, the level of stimulation being below an excitability threshold of alpha neurons innervating the at least one muscle, wherein the electrical impulse acts upon a gamma loop.

28. The system of claim 27, wherein the electrical impulse acts upon one or more gamma neurons located within the gamma loop.

29. The method of claim 28, wherein the electrical impulse acts upon one or more afferent neurons located within the gamma loop.

\* \* \* \* \*